United States Patent
Sanchez et al.

(10) Patent No.: US 10,617,299 B2
(45) Date of Patent: Apr. 14, 2020

(54) TELEHEALTH CART THAT SUPPORTS A REMOVABLE TABLET WITH SEAMLESS AUDIO/VIDEO SWITCHING

(71) Applicant: INTOUCH TECHNOLOGIES, INC., Goleta, CA (US)

(72) Inventors: Daniel Steven Sanchez, Summerland, CA (US); Gary S. Douville, Santa Barbara, CA (US); Shuodan Chen, Goleta, CA (US); James Rosenthal, Santa Barbara, CA (US); Andrew Kirchhoff, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 15/965,623

(22) Filed: Apr. 27, 2018

(65) Prior Publication Data
US 2019/0328229 A1 Oct. 31, 2019

(51) Int. Cl.
*A61B 5/00* (2006.01)
*H04N 7/14* (2006.01)
*G16H 40/67* (2018.01)

(52) U.S. Cl.
CPC .......... *A61B 5/0022* (2013.01); *G16H 40/67* (2018.01); *H04N 7/144* (2013.01)

(58) Field of Classification Search
CPC ....... A61B 5/0022; G16H 40/67; H04N 7/144
See application file for complete search history.

(56) References Cited

U.S. PATENT DOCUMENTS

| | | | |
|---|---|---|---|
| 8,182,426 B2 | 5/2012 | Zhao et al. | |
| 9,877,699 B2 | 1/2018 | Chiang et al. | |
| 2005/0288571 A1* | 12/2005 | Perkins | A61B 5/0002 600/407 |
| 2009/0270727 A1 | 10/2009 | Zhao et al. | |
| 2012/0306994 A1* | 12/2012 | Schwartz | G06F 19/3418 348/14.08 |
| 2014/0121524 A1 | 5/2014 | Chiang et al. | |
| 2015/0190927 A1* | 7/2015 | Sutherland | H04W 4/70 700/259 |
| 2015/0277492 A1* | 10/2015 | Chau | G06F 1/1632 361/679.43 |

(Continued)

FOREIGN PATENT DOCUMENTS

JP 2013017707 A 1/2013

*Primary Examiner* — Stella L. Woo

(57) ABSTRACT

A two-way audiovisual communication device with multiple audio and video subsystems. In one embodiment, the device includes a wheeled cart that supports a dock for a tablet computing device that includes a tablet camera, a tablet display, and a tablet microphone. The device also includes a cart camera, a cart speaker, and a cart microphone. The device may be coupled to a network and accessible to other devices on the network to allow a two-way audiovisual session to take place between remote parties. The device may operate in two modes: In a first mode, the tablet is mated with the dock and the remote device receives video from the pan-tilt-zoom camera and audio from the cart microphone. In a second mode, the tablet is removed from the dock and the remote device receives video from the tablet camera and audio from the tablet microphone. In both modes, the tablet monitor displays video from the remote device.

20 Claims, 5 Drawing Sheets

(56) References Cited

U.S. PATENT DOCUMENTS

2015/0305086 A1\* 10/2015 Uttley .................. B62B 1/12
                                                                         280/652
2016/0328532 A1\* 11/2016 Rieder ............... G06F 19/3418
2018/0168548 A1    6/2018 Chiang et al.

\* cited by examiner

TELEHEALTH CART THAT SUPPORTS A REMOVABLE TABLET WITH SEAMLESS AUDIO/VIDEO SWITCHING

BACKGROUND

Telemedicine, also referred to as telehealth, generally refers to the use of technology to enable physicians or other healthcare providers to examine and treat or recommend treatment for a remotely located patient. Although telemedicine can be practiced using technology as simple as a telephone, the telemedicine solution market today includes devices and software having a wide range of sophistication.

The range of solutions generally intends to satisfy the functional and economic requirements of telemedicine encounters in different types of settings with varying levels of acuity. For example, smartphones, tablets, or laptop computers with basic audiovisual capabilities may be sufficient for a patient to consult with their doctor on treating a cold or behavioral health issues. These types of devices, however, may be insufficient in a higher acuity setting such as a hospital emergency department, intensive care unit, or specialty clinic, where the remote physician may require more capable video or imaging devices and/or the ability to monitor data from peripheral medical devices in real time. Other settings where telemedicine is practiced may present other unique requirements. Thus, the telemedicine solution market is replete with disparate devices and software that seek to satisfy the varied requirements of many different telehealth encounter settings.

SUMMARY

It would be desirable to provide a telemedicine device with broader suitability by integrating the simplicity and familiarity of a smartphone, tablet, or laptop, with a more sophisticated telemedicine system that facilitates use in higher-acuity settings and includes enhanced audio and video systems as well as the ability to connect to a variety of medical peripherals.

To achieve these ends, one aspect of the disclosure includes a telemedicine system comprising a cart that supports a dock and a cart camera. The dock is adapted to receive a tablet device that includes a tablet camera. The system also includes a remote device communicatively coupled to the tablet via a network. The remote device includes a display device that displays video captured by the cart camera when the tablet is coupled to the dock and displays video captured by the tablet camera when the handheld computing device is decoupled from the dock. The system may display video from the remote station on the tablet display when then tablet is docked and when it is undocked.

DETAILED DESCRIPTION

The following disclosure includes a telemedicine system including a cart that supports a dock and audio and video hardware. The dock is configured to receive a tablet computing device that can connect to and establish a two-way audiovisual session with a remote station. When the tablet is docked, the tablet is connected to the cart's audio and video hardware and the tablet may stream audio and video from the cart A/V hardware to the remote station. When the tablet is undocked, the tablet may stream audio and video from the tablet's onboard A/V hardware to the remote station. The cart may also include peripheral ports that allow the tablet to stream peripheral data to the remote station when the tablet is docked.

Figure 1:
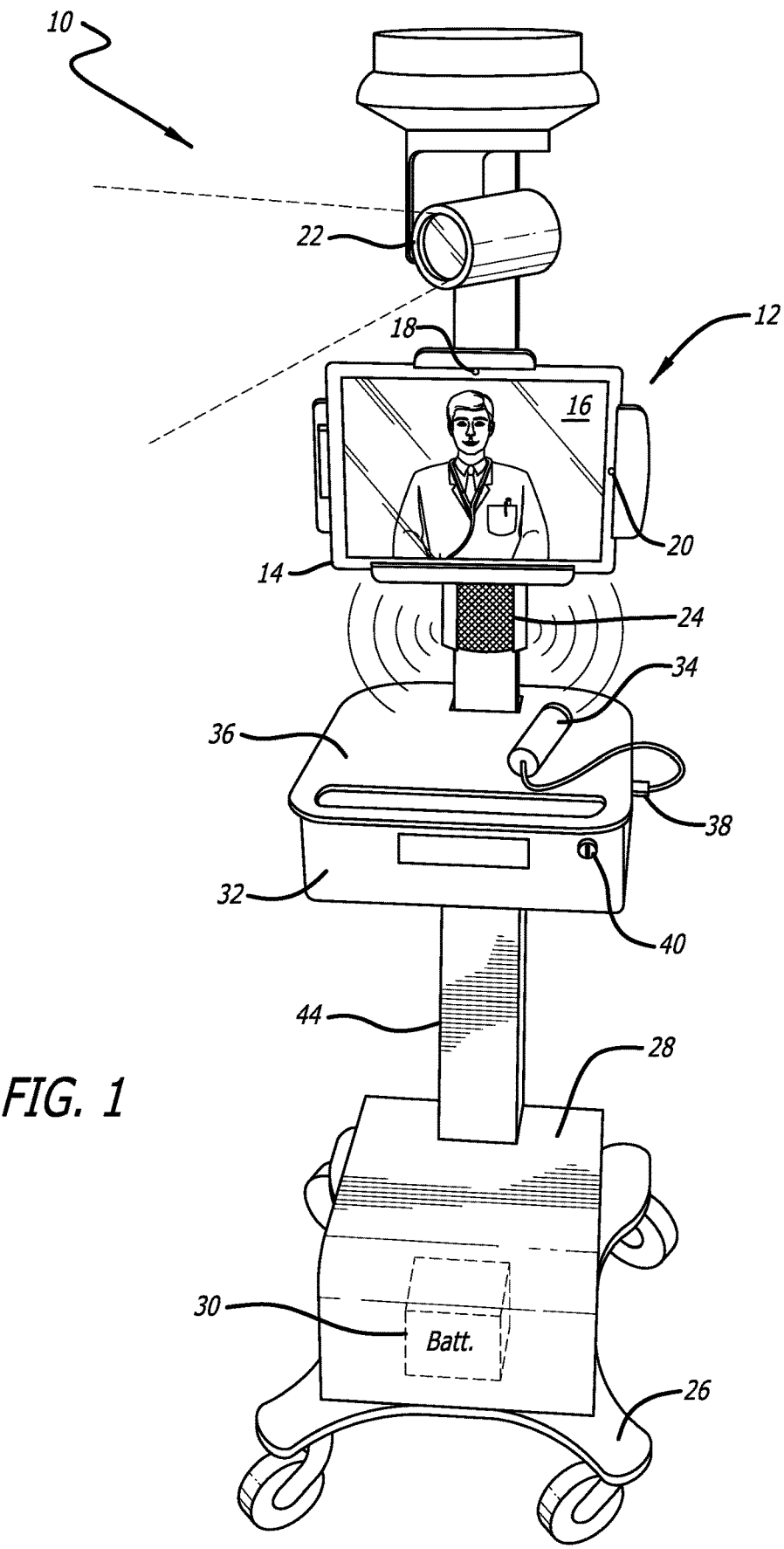
FIG. 1 illustrates an example of a telemedicine system in accordance with the disclosure.

With reference to the drawings, FIG. 1 illustrates a front view of an exemplary telemedicine cart 10 that forms part of a telemedicine system in accordance with the disclosure. The cart 10 may support a dock 12 that can be mated with a tablet computing device 14. The tablet computing device 14 may include at least one built-in display 16, camera 18, speaker 20, and microphone (not shown). The cart 10 may also support a cart camera 22 and a cart audio module 24, which may include both a speaker and a microphone (not shown). The cart audio module 24 may be incorporated as a single device as illustrated in FIG. 1 or as separate speaker and microphone modules.

The cart 10 may include a wheeled base 26 that supports a housing 28 that encloses a battery 30 and/or other electrical components. The cart 10 may also support a drawer 32 that can be used to store one or more medical peripherals or other accessories that may be needed during a session. FIG. 1 illustrates an exemplary medical peripheral 34 resting on a work surface 36 above the drawer 32 and coupled to the cart 10 via a peripheral port 38. The drawer 32 may include a lock 40 to prevent removal of items stored therein. Examples of medical peripherals that may be connected to the peripheral port include a stethoscope, otoscope, dermal camera, exam camera, vitals monitor, portable ultrasound, etc.

The tablet computing device 14 executes an application that allows a remote device (not shown) to establish a two-way audiovisual session with the tablet. The remote device executes a similar application to communicate with the tablet. The application may be a telemedicine application that allows for two-way audiovisual communication, remote camera control, access to medical records and imagery, and other features that facilitate a remote consultation between a healthcare provider and a patient. The remote device could be a laptop or desktop computer, tablet, smartphone, video-conferencing terminal, or any other device suitable for conducting a two-way audiovisual communication session. During the session, the tablet display 16 displays video captured by a camera of the remote device. Typically, during a telemedicine session, a physician uses the remote device to consult with a patient located in the vicinity of the cart 10. In this scenario, and as illustrated in FIG. 1, the physicians image, captured by the camera of the remote device, may be displayed on the tablet display 16 so the patient can see the physician. While the tablet is mated with the dock 12, the cart camera 22 is used to capture video of the patient, which is communicated to and displayed at the remote device so the physician can see the patient. Similarly, while the tablet 10 is mated with the dock 12, audio captured by a microphone of the cart audio module 24 may be streamed to and reproduced by a speaker of the remote device, while audio captured by a microphone of the remote device is streamed to and reproduced by a speaker of the cart audio module 24. In this way, the remote physician and the patient in the vicinity of the cart 10 can both see and hear each other.

Figure 2:
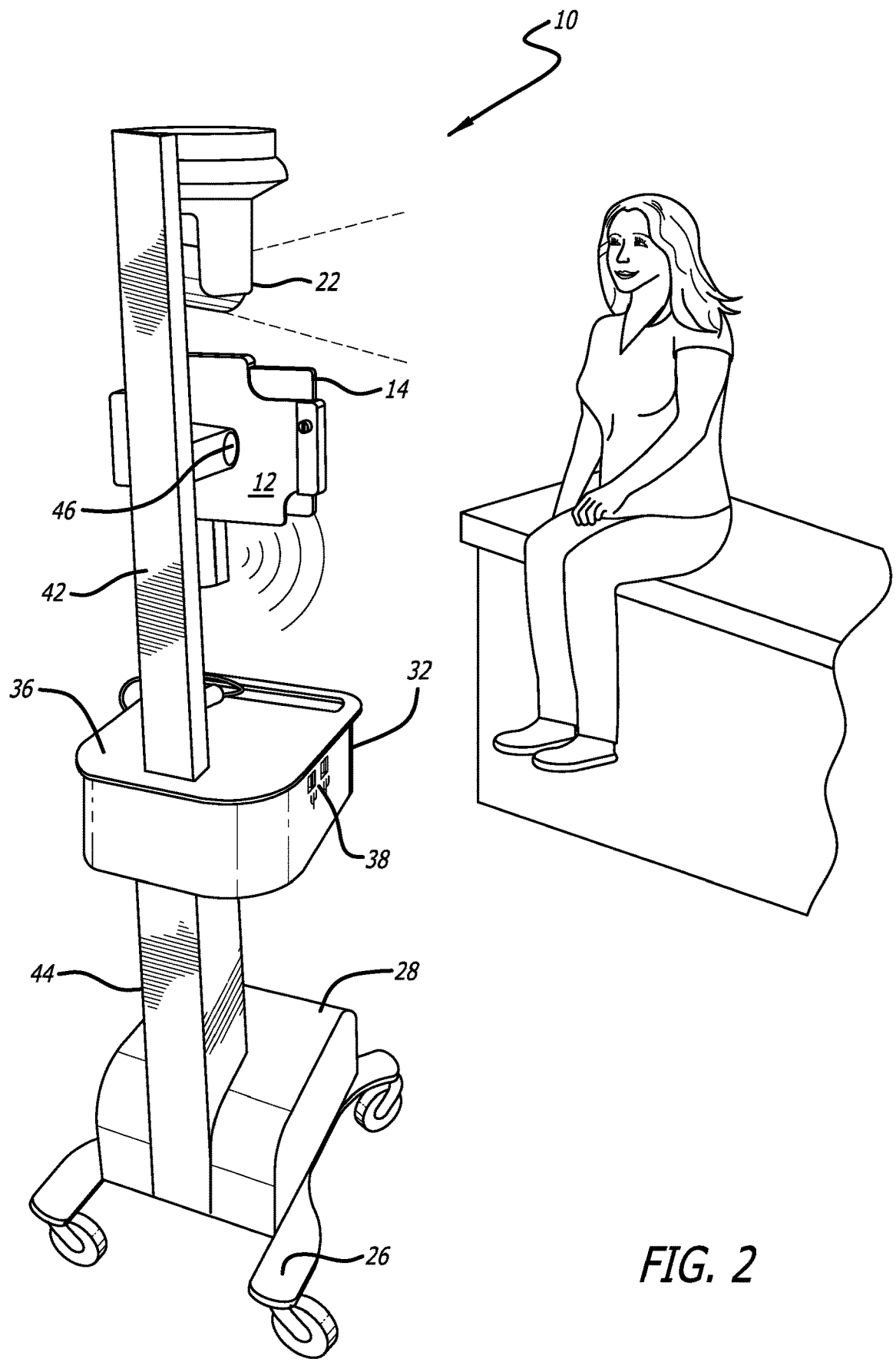
FIG. 2 illustrates an example of a telemedicine system in accordance with the disclosure in use during a session with a patient.

FIG. 2 illustrates a rear view of an exemplary telemedicine cart 10 in accordance with the disclosure. One or both of the dock 12 and the cart camera 22 may be supported by an upper column 42 connected to the base 26 via a lower column 44. The drawer 32 and the work surface 36 may also be coupled to the lower column 44. The height of either or both the upper and lower columns 42, 44 may be adjustable to allow the height of the cart camera 22, the dock 12, the work surface 36, and the drawer 32 to be adjusted. By way of example, the height of the cart camera 22 and the dock 12 may be adjustable in a range of two feet to seven feet. This allows the height of the tablet 14 and the cart camera 22 to be adjusted to suit a variety of situations in which the patient may be standing, seated, or lying on a gurney, patient bed, or floor. The dock 12 may be coupled to the upper column 42 via a hinge 46 that allows a tilt angle of the dock and the tablet to be adjusted. By way of example, the dock 12 may be tilted in a range of +/−60 degrees about a line drawn parallel to the floor. FIG. 2 additionally illustrates several peripheral ports 38 on the side of the drawer 32 that can be used to attach a variety of medical or other peripheral devices to the telemedicine system.

Figure 3:
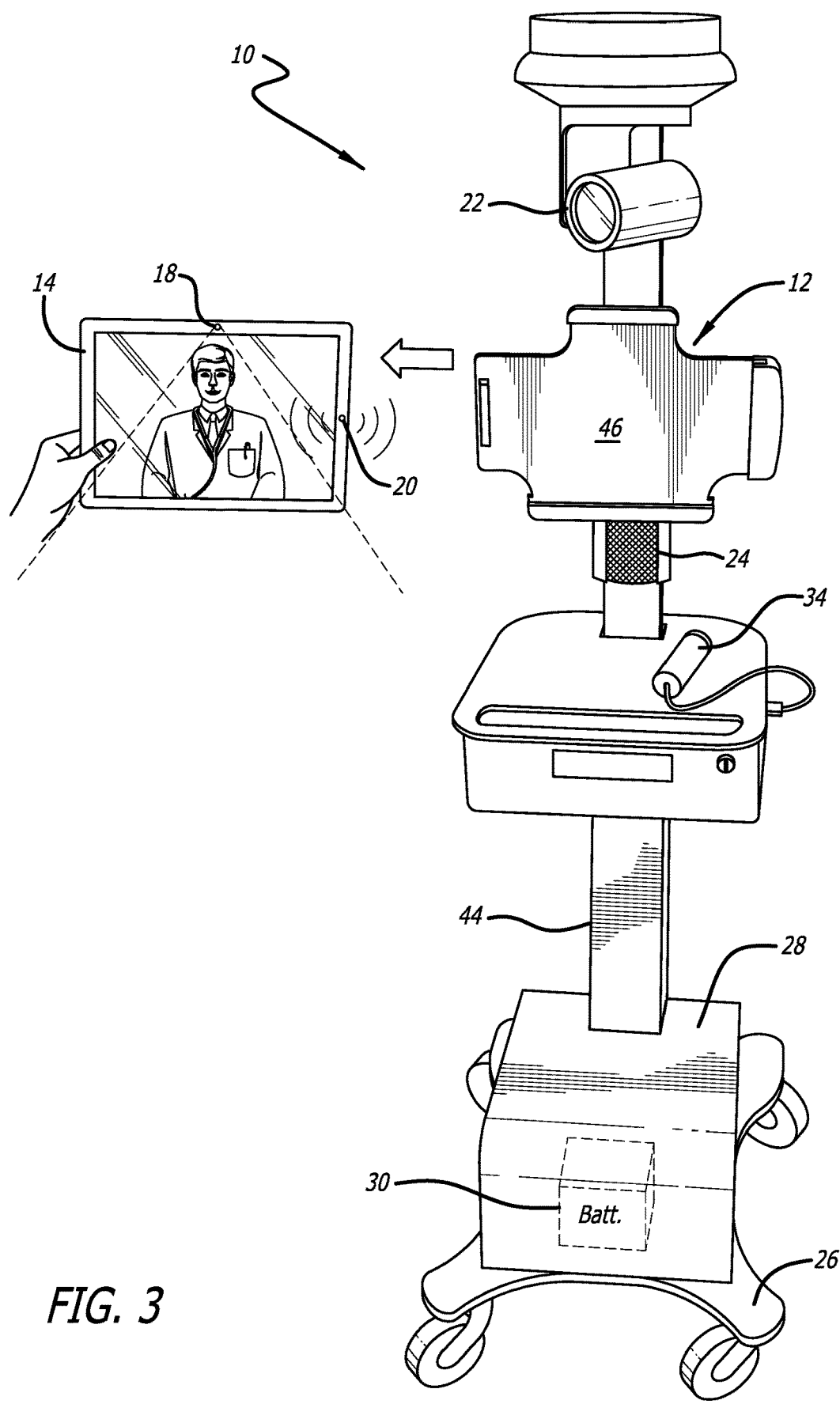
FIG. 3 illustrates an example of a telemedicine system in accordance with the disclosure with the tablet device removed from dock.

FIG. 3 illustrates a view of an exemplary telemedicine cart 10 with the tablet 14 removed from the dock 12. As described above with respect to FIGS. 1 and 2, when the tablet 14 is mated with the dock 12, audio and video of the patient are captured by the cart camera and a microphone of the cart audio module 24, and physician audio from the remote station is reproduced by a speaker of the cart audio module 24. When the tablet 14 is removed from the dock 12, the session continues uninterrupted, but the audiovisual session switches automatically to the audio and video subsystems of the tablet 14. Thus, while the tablet 14 is undocked, the remote device receives video of the patient from the tablet camera 18 and audio of the patient from the tablet microphone (not shown). Similarly, audio from the remote device is reproduced by the tablet speaker 20. This allows a patient, or someone in the vicinity of the cart 10, to remove the tablet 14 from the dock 12 during a session and continue the session with the tablet 14 in his or her hands, while moving around or to another room, and/or at a desk or in a chair away from the cart 10 itself. In general, the system enables a person in the vicinity of the cart 10 to carry on a session wherever the tablet 14 can be moved to and its network connection maintained. Alternatively, the session can be initiated while the tablet 14 is not in the dock 12, and the tablet 14 can later be mated with the dock 12 during the session to enable the remote physician to access audio and video from the cart camera 22 and cart audio module 24, as well as images, audio, and/or other data from one or more medical peripherals 34 coupled to the cart 10. Regardless of the location of the tablet 14 when the session begins, the tablet 14 can be docked or undocked as desired to leverage the portability of the tablet 14 or the enhanced audiovisual and peripheral capabilities of the cart 10 as needed, without interrupting the existing session with the remote physician.

Figure 4:
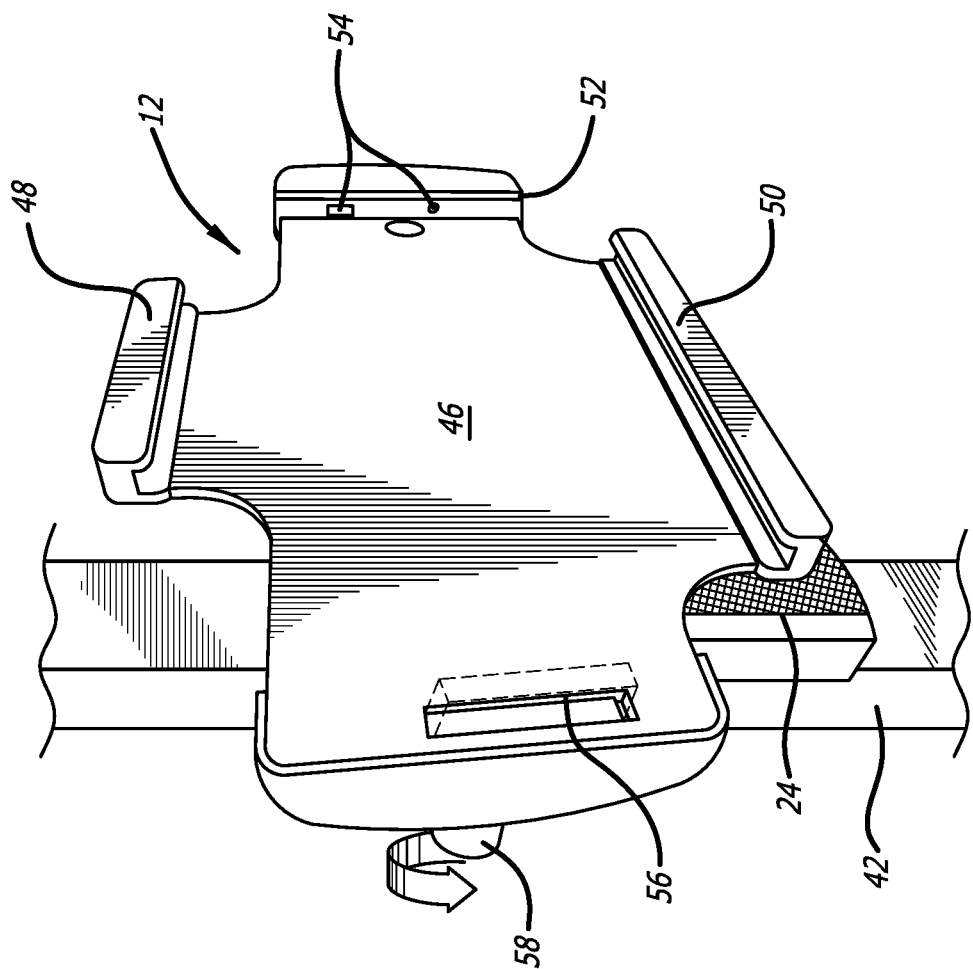
FIG. 4 is a detailed view of an example of a dock in accordance with the disclosure.

FIG. 4 illustrates a detailed view of an example of the dock 12. The dock 12 may be coupled to the upper column 42 via a hinge (not shown) to allow the dock 12 to be tilted up and down, as described above. The hinge may also allow the dock 12 to be panned to the left and right. The dock 12 may include a frame 46 and upper 48 and lower 50 horizontal channel guides adapted to receive and secure the tablet in the dock 12. The dock may also include a vertical stop 52 coupled to one end of the frame 46 to guide and position the tablet when it is slid into the dock 12. The vertical stop 52 may include electrical contacts 54 adapted to engage electrical contacts on the tablet. For example, the vertical stop 52 may include a data plug and a power plug that mate with a data jack and power jack, respectively, on the tablet when the tablet is seated in the dock 12. The dock 12 may additionally include a retractable tab mechanism 56 that can be retracted to allow the tablet to be slid in and out of the dock 12 or extended to prevent removal of the tablet while it is seated in the dock 12. The retractable tab 56 may be extended or retracted by actuating a key lock 58 mounted on the frame 46 of the dock 12. Those skilled in the art will recognize that the location of any power and/or data plugs on the dock 12 will depend on the location of their corresponding jacks on the housing of the tablet.

Figure 5:
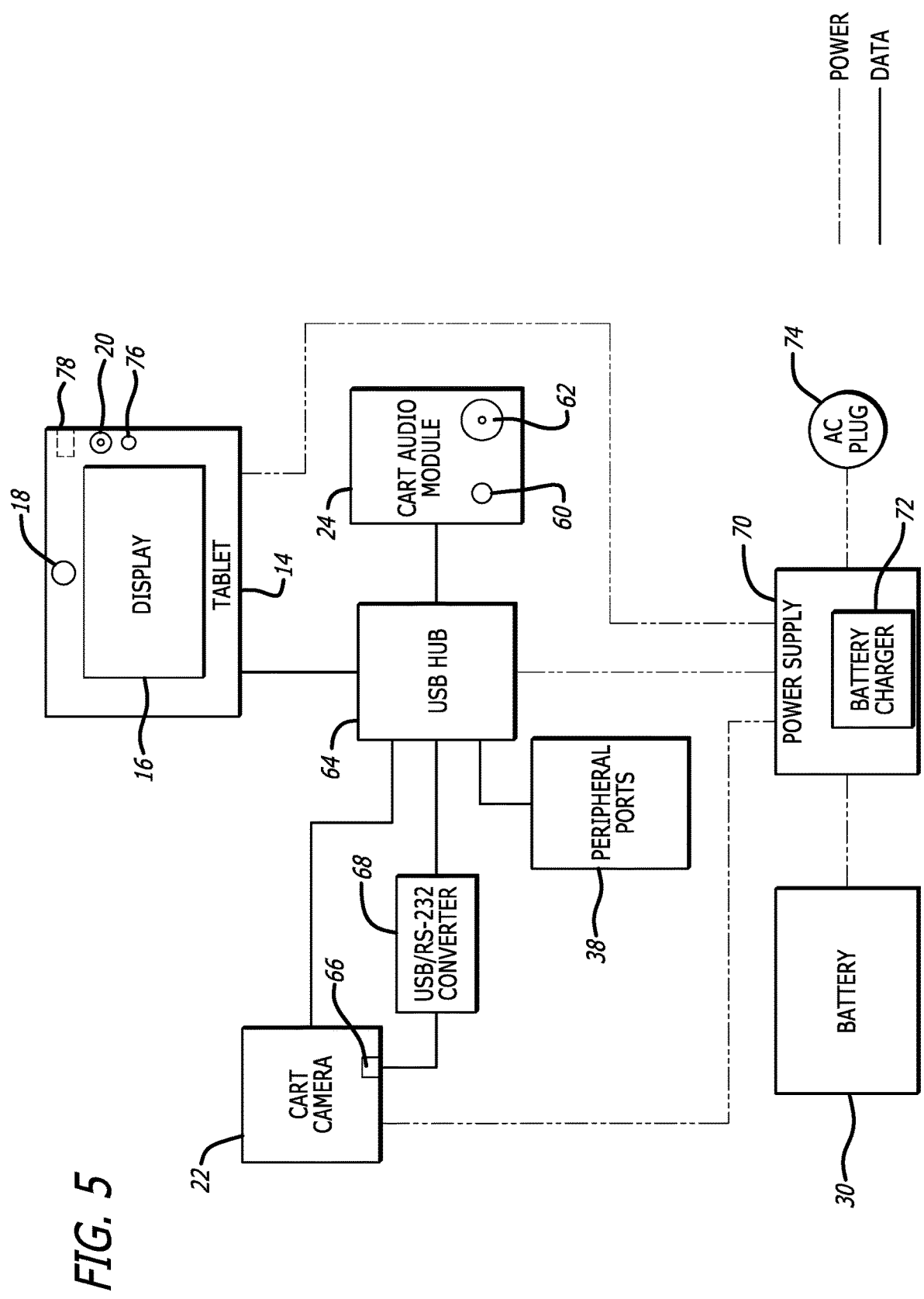
FIG. 5 is a block electrical diagram of a telemedicine system in accordance with the disclosure.

FIG. 5 is an electrical block diagram of the various components of an exemplary telemedicine cart in accordance with the disclosure. The system may include a tablet computing device 14, a cart camera 22, and a cart audio module 24, which may include a microphone 60 and a speaker 62. An example of a tablet suitable for use in the described system is the SURFACE PRO tablet marketed by the MICROSOFT CORP. of Redmond, Wash. The cart camera 22 may take the form of a pan-tilt-zoom or ("PTZ") camera. An example of a PTZ camera suitable for use in the described system is the TELYCAM Model TLC300 marketed by TELECAM TECHNOLOGY, CO. An example of a suitable cart speaker and microphone module 24 is the PHOENIX AUDIO DUET-PCS Desktop Speakerphone. Although the microphone 60 and speaker 62 are illustrated as incorporated into a single audio module 24, it is to be appreciated that the microphone 60 and speaker 62 may be embodied as separate components. The cart may also include one or more universal serial bus ("USB") peripheral ports 38 that allow for the connection of peripheral medical devices or other external devices to the system. Each of the tablet 14, the cart camera 22, the cart audio module 24, and the USB peripheral ports 38 may be coupled to and communicate with each other over a USB interface via a USB hub 64.

Depending on the capabilities of the cart camera 22, the cart camera may also include a control interface 66. The camera control interface may be implemented using a serial data interface such as RS-232 and allow for enhanced camera control. In order to enable these enhanced camera controls, the cart may include a USB/RS-232 converter 68 interposed between the control interface 66 and the USB hub module via USB. This allows enhanced camera controls to flow from the tablet 14 to the camera control interface 66.

The cart may additionally include a battery 30 coupled to a power supply 70 that includes a battery charger 72. The power supply 70 may include an AC cord and/or plug 74 that receives line voltage from a standard wall socket to power the cart and/or charge the cart battery 30. The battery 30 allows the cart to be wheeled to and used at a location for hours or days where no wall socket is available. Some components, such as the cart camera 22, the USB hub 64, and the tablet 14, may support dedicated connections to the power supply 70, illustrated with dotted lines in FIG. 5. Other components, such as the cart audio module 24, the USB/RS-232 converter 68, and the peripheral ports 38, may be powered using power drawn from other components via their data (e.g., USB) connections, illustrated with solid lines in FIG. 5. It is to be appreciated the components shown as having or not having dedicated power connections is only illustrative and any combination, including all or none, of the components may use (or not use) a dedicated power connection.

The cart may leverage the tablet's 14 own wireless network adapter (not shown) to connect to the Internet. For example, the tablet 14 establishes a connection with the Internet via its own WiFi or cellular adapter (or both) and the application running on the tablet communicates with the audio, video, and peripheral hardware of the cart to stream the audio, video, and peripheral data therefrom over the network connection to the remote station. It is to be appreciated that the cart could alternatively or additionally have onboard wired and/or wireless network adapters that could be accessed by the application executing on the tablet to communicate with the remote station via the Internet.

The tablet may be configured to remain active and executing the application at all times. This ensures that the tablet, the cart, and the system in general are available to accept an incoming request to establish a telemedicine session at any time, which is preferable in a medical setting where emergent situations are common.

During the telemedicine session, the application on the tablet is configured to detect whether a cart camera, cart microphone, and cart speaker are available to stream audio and video data to the tablet via the USB interface. If so, the application streams the audio and video data from the cart audio and video hardware to the remote station via the network connection. Likewise, in this case, the application will reproduce audio received from the remote station via the cart speaker. On the other hand, if the application cannot receive audio and video from the cart audio/video hardware, the tablet will stream audio and video data from the tablet's onboard camera and microphone to the remote station. Likewise, in this case, the tablet will reproduce audio received from the remote station via the tablet's onboard speaker. In either case, video received from the remote station is displayed on the tablet monitor.

In one embodiment, the switching of audio and video sources by the application may be implemented by setting the default audio and video hardware in the tablet operating system. For example, the application may periodically poll or continuously listen to the tablet's USB interface for the presence of certain devices indicative of the tablet being docked. That presence of one or more, or any combination of, the following devices may be used by the application to determine whether the tablet is docked: battery charger 72, power supply 70, cart camera 22, cart audio module 24, peripheral ports 38, or any other suitable device.

When the application senses that the tablet is docked, it may be configured to set the default microphone and speaker in the tablet operating system to the microphone and speaker of the cart audio module 24. Similarly, the application may be configured to set the default camera in the tablet operating system to the cart camera 22. In one embodiment, the application may force (or repeatedly set) the cart audio module as the default speaker and microphone to prevent the operating system from selecting another external speaker/microphone system (such as a headset) that may be plugged into the tablet while the tablet is docked.

When the application senses that the tablet is undocked, the application may be configured to allow the tablet operating system to set the default microphone and speaker. In this way, when the tablet is undocked, the audio may be captured and reproduced by the tablet's built-in microphone and speaker, or an external microphone and speaker that the user may choose to plug into the tablet (e.g., a headset microphone and speaker set). Similarly, when the tablet is undocked, the application may allow the operating system to set the default camera, which may be the tablet's built-in camera. If the tablet includes multiple on-board cameras (such as a forward-facing camera and a rear-facing camera), the application may alert the corresponding application at the remote device to the presence of multiple cameras, which may then provide the user of the remote device with the option to select to display video from either or both of the tablet cameras.

As described above, while the tablet is docked, the application may set the default camera to the cart camera. However, if the application detects the presence of additional cameras or other devices connected to the peripheral ports 38 on the cart, the application running on the tablet may alert the application running on the remote device of the presence of the additional cameras or other devices. In this scenario, the application at the remote device may provide the user of the remote device with the option to select to display video, image, or other data from one or more of the peripheral devices. The user's selection may then be communicated back to the application running on the tablet to control which device's video or other data is streamed back to the remote device. The selected video or other data may be displayed instead of or in addition to (as a multi-tiled or split screen display) video from the cart camera.

As discussed above, regardless of the state of the tablet (i.e., docked or undocked) when the session begins, the tablet can be docked or undocked any number of times thereafter and, each time, the application will automatically switch to streaming audio and video to and from the cart hardware or the tablet's onboard audio and video hardware accordingly such that the audio video session may continue uninterrupted.

In an alternative embodiment, the cart could additionally include one or more display devices that could be used, alternatively or additionally, to display video received from the remote station. In this embodiment, as with the embodiment described above, either the tablet display or the cart display may be used to display the video from the remote station depending on whether the tablet is seated in the dock.

During the session, the application may be configured to read and display and the tablet display one or more physiological parameters received from one or more medical monitoring device connected to the cart's peripheral ports. In one embodiment, the cart may be placed in a clinic where a patient is scheduled to have a consultation with a remote physician. In this case, a nurse or medical assistant may capture patient vitals, such as temperature, heart rate, blood pressure, and blood oxygen saturation using one or more peripheral monitoring devices connected to the cart. The patient vitals may be displayed on the tablet display for verification by the nurse. When the nurse is satisfied that the patient vitals are accurate, he or she may tap a button on the tablet display or issue a verbal command that instructs the application to transmit a message to the remote device including the patient vitals data and an alert that the patient is ready for the remote consultation to begin. The remote physician may then initiate the two-way audiovisual session with the cart from the remote device.

Additionally, as will be appreciated by one of ordinary skill in the art, principles of the present disclosure may be reflected in a computer program product on a computer-readable storage medium having computer-readable program code embodied in the storage medium, the computer-readable program code executable by a processor. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

While certain exemplary embodiments have been described and shown in the accompanying drawings, it is to be understood that such embodiments are merely illustrative and not restrictive on the broader disclosure, and that this disclosure not be limited to the specific constructions and arrangements shown and described, since various other modifications may occur to those ordinarily skilled in the art.

What is claimed is:

1. A telemedicine system comprising:
    a cart that supports a cart camera and a dock that is electrically coupled to the cart camera and adapted to receive a tablet device that includes a tablet camera; and
    a remote device communicatively coupled to the tablet via a network, the remote device including a display device that displays video received from the tablet device during a communication session, wherein the video received from the tablet device is automatically switched, without interrupting the communication session, between video from the cart camera and video from the tablet camera depending on whether the tablet is coupled to the dock such that the display device displays video captured by the cart camera when the tablet is coupled to the dock and the display device displays video captured by the tablet camera when the tablet device is decoupled from the dock and the cart camera.

2. The system of claim 1, wherein the dock includes a plurality of electrical contacts that mate with the tablet when the tablet device is coupled to the dock.

3. The system of claim 2, wherein the cart further includes a power system that is coupled to tablet via one or more of the plurality of electrical contacts when the tablet is coupled to the dock.

4. The system of claim 3, wherein the power system includes a battery.

5. The system of claim 3, wherein the power system includes a battery charger.

6. The system of claim 3, wherein the power system includes an AC power plug attached to the cart via a power cord.

7. The system of claim 2, wherein the cart camera is coupled to the tablet via one or more of the plurality of electrical contacts when the tablet is coupled to the dock.

8. The system of claim 2, wherein the cart supports a cart speaker and a cart microphone, the cart speaker reproduces audio captured by a microphone of the remote device and the remote device includes a speaker that reproduces audio captured by the cart microphone.

9. The system of claim 8, wherein the cart speaker and the cart microphone are coupled to the tablet via one or more of the plurality of electrical contacts when the tablet is coupled to the dock.

10. The system of claim 8, wherein the tablet includes a tablet speaker and a tablet microphone, wherein, when the tablet is decoupled from the dock, the tablet speaker reproduces audio captured by a microphone of the remote device and the remote device includes a speaker that reproduces audio captured by the tablet microphone.

11. The system of claim 1, wherein the tablet device includes a display device, the remote device includes a camera, and the tablet display device displays video captured by the remote device camera.

12. The system of claim 11, wherein the tablet display device is a touchscreen.

13. The system of claim 12, wherein the tablet display device displays one or more physiological values received via a medical peripheral coupled to the tablet.

14. The system of claim 1, wherein the cart camera is a pan-tilt-zoom camera and can be controlled by a user input via the remote device.

15. The system of claim 1, wherein the dock includes a latching mechanism for securing the tablet when coupled to the dock.

16. The system of claim 15, wherein the latch includes a lock.

17. The system of claim 1, wherein the cart supports a work surface.

18. The system of claim 1, wherein the cart supports a drawer.

19. The system of claim 1, wherein the height of at least one of the dock and the cart camera is adjustable.

20. The system of claim 1, wherein the cart includes a peripheral communication port that can be coupled to peripheral device and the tablet via a communication bus.

* * * * *